United States Patent [19]
Stedham

[11] Patent Number: 5,840,047
[45] Date of Patent: Nov. 24, 1998

[54] SENSOR DEVICE FOR MONITORING A PROSTHETIC DEVICE

[75] Inventor: David M. Stedham, Reno, Nev.

[73] Assignee: Prosthetic Sensing Technologies, LLC, Reno, Nev.

[21] Appl. No.: 632,965

[22] Filed: Apr. 16, 1996

[51] Int. Cl.⁶ .................. A63B 5/103; A61F 2/60
[52] U.S. Cl. .............. 600/587; 623/33; 623/34; 600/595
[58] Field of Search .................. 623/24, 33, 36, 623/34; 73/172; 600/595, 587

[56] References Cited

U.S. PATENT DOCUMENTS

| | | | |
|---|---|---|---|
| 3,791,375 | 2/1974 | Pfeiffer | 73/172 X |
| 3,974,491 | 8/1976 | Sipe | 73/172 |
| 4,767,973 | 8/1988 | Jacobsen | 318/652 |
| 5,197,488 | 3/1993 | Kovacevic | 600/595 |
| 5,246,463 | 9/1993 | Giampapa | 623/24 |
| 5,253,656 | 10/1993 | Rincoe et al. | 73/172 X |
| 5,323,658 | 6/1994 | Fullen et al. | 73/172 |
| 5,326,363 | 7/1994 | Aikens | 623/20 |
| 5,549,709 | 8/1996 | Casper | 623/24 |
| 5,619,186 | 4/1997 | Schmidt | 73/172 X |
| 5,678,448 | 10/1997 | Fullen | 73/172 |

Primary Examiner—Michael A. Brown
Assistant Examiner—William LaMarca
Attorney, Agent, or Firm—Michael J. Striker

[57] ABSTRACT

The sensor and alarm system for monitoring a relative position of a prosthetic device with respect to the residual portion of an amputee's limb includes a battery power supply; a proximity sensor for generating a position signal indicative of the relative position of the prosthetic device and the residual portion in the prosthetic device near the residual portion, and an alarm device for signaling when the prosthetic device is located in an injurious position or positions.

11 Claims, 5 Drawing Sheets

SENSOR DEVICE FOR MONITORING A PROSTHETIC DEVICE

BACKGROUND OF THE INVENTION

The present invention relates to a sensor device for monitoring a prosthetic device, especially an artificial limb, and, more particularly to a sensor and alarm system for monitoring the position of a residual portion of an amputee's limb relative to a prosthetic device connected to the amputee's limb.

Prosthetic devices have been used for many years to replace a portion of a limb, e.g. a leg, which has been amputated because of trauma or disease. Each prosthetic device is custom fit to embrace the amputee's residual limb in order to provide a comfortable and safe fit, allowing the amputee to properly use the prosthetic device. Though the initial fit of the prosthetic device may be correct, during a normal day the fit of the prosthetic device will change. This is due to factors such as normal shrinkage of the limb as the day progresses, a higher degree of physical exertion than average, perspiration, etc. When this occurs, adjustment of the fit of the prosthetic device is required to avoid possible injury, such as blistering, abrasions, bruising, etc. These injuries may result in the inability of the amputee to wear the prosthetic device until the injuries heal sufficiently. In extreme cases, the residual limb can be so severely injured, that further amputation and suffering results.

It is up to the amputee to initiate a change in fit of the prosthetic device as a normal day progresses. Often however, due to the nature of the disease or trauma which resulted in the amputation, or due to the amputation itself, there is a highly reduced sense of feel on the skin of the residual limb. This may make it very difficult or impossible to sense that adjustment of the fit of the prosthetic device is immediately necessary to avoid injury. Additionally, in times of increased physical exertion, the amputee may not realize that adjustment is required.

SUMMARY OF THE INVENTION

It is an objective of the present invention to provide a sensor and alarm system for monitoring a prosthetic device connected with a residual portion of an amputee's limb, particularly a leg of the amputee, which produces an alarm signal when the prosthetic device is in an undesirable position relative to the residual portion of the amputee's limb which might result in injury to the residual portion.

It is not an objective of the present invention to provide a proximity sensor. This is well know and commonly utilized technology.

According to the invention the sensor system for monitoring a position of a prosthetic device fitted to a residual portion of a limb of an amputee comprises a battery power supply, one or more proximity sensor means for generating a signal indicative of a relative position of the prosthetic device and the residual portion of the limb, the one or more proximity sensor means being held in the prosthetic device at a position(s) adjacent to the residual portion of the amputee's limb and being electrically connected to the battery power supply and including alarm means for signaling the amputee when the prosthetic device is located in that at least one position.

In preferred embodiments of the invention the battery power with the alarm means are mounted on the prosthetic device near the proximity sensor means.

The proximity sensor means is located adjacent to an area of potential injury such as next to the center of the residual portion of the amputee's limb in a preferred embodiment of the invention, but it can also be located laterally displaced from the center of the residual portion.

In a preferred embodiment of the invention, the battery power supply, the alarm means and the proximity sensor means can be integrated in a single device or housing, advantageously a chip, or as individual discrete elements.

In preferred embodiments of the invention the proximity sensor means is a standard commercially available capacitive proximity sensor, such as Honeywell Micro Switch product Part Number 972CP8TM-A13P-L.

In a preferred embodiment of the invention the proximity sensor means advantageously can also include any combination of the following types of standard commercially available proximity sensors: photoelectric sensors including Infra Red and laser diode sensors, and ultrasonic sensors. The standard commercial proximity sensors commonly have an adjustable set point. When the position of the residual limb reaches the set point, the sensor initiates a signal state change, which then is used to initiate the alarm output.

In one particularly advantageous form of the sensor device, a capacitive proximity sensor determines when the residual portion of an amputee's leg moves into a position, relative to a prosthetic device, that would likely cause injury to the residual limb, and then signals the amputee to take corrective action to adjust the fit of the prosthetic device before any injury occurs.

BRIEF DESCRIPTION OF THE DRAWING

The objects, features and advantages of the present invention will now be illustrated in more detail by the following detailed description, reference being made to the accompanying drawing in which.

DESCRIPTION OF THE PREFERRED EMBODIMENTS

Figure 1:
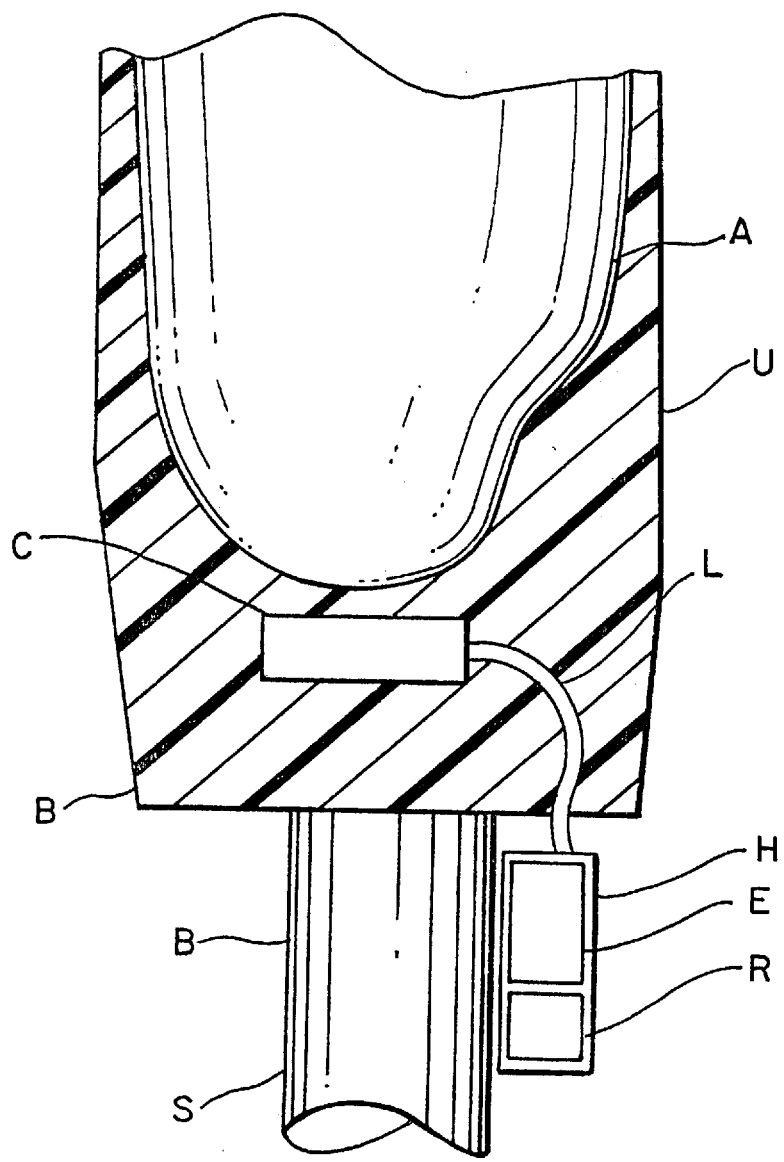
FIG. 1 is a cross-sectional view of one embodiment of a sensor device for monitoring the relative position of a residual portion of an amputee's leg relative to a prosthetic device connected to the amputee's leg.

FIG. 1 shows a first embodiment of the sensor system according to the invention. A prosthetic leg device B is fitted to a residual portion A of an amputee's leg. The prosthetic device B has an upper member U which embraces the curved lower part of the residual portion A. If the residual portion A takes certain positions in the upper member U, the prosthetic device can injure the residual portion.

In the embodiment shown in FIG. 1, a capacitive proximity sensor C is embedded or held in a center of the upper member U next to the lower end of the residual portion A of the amputee's leg. A remote battery power supply with an alarm means R housed in Housing H and mounted on an end portion or the stem S of the prosthetic device B attached to the upper member C. The cable line L connects the proximity sensor C electrically to the remote battery power supply E so that it can receive electrical power and feed the output position signal to the alarm means R. The operating set point of the sensor C, is adjusted to result in a change in signal state when the residual portion of the amputee's limb A, enters an injurious position with respect to the upper member U of the prosthetic device B. This change in signal state, through the power provided by the remote battery power supply E and transmitted by cable line L, supplies power to the alarm means R, resulting in the alarm warning to the amputee to take corrective action.

Figure 2:
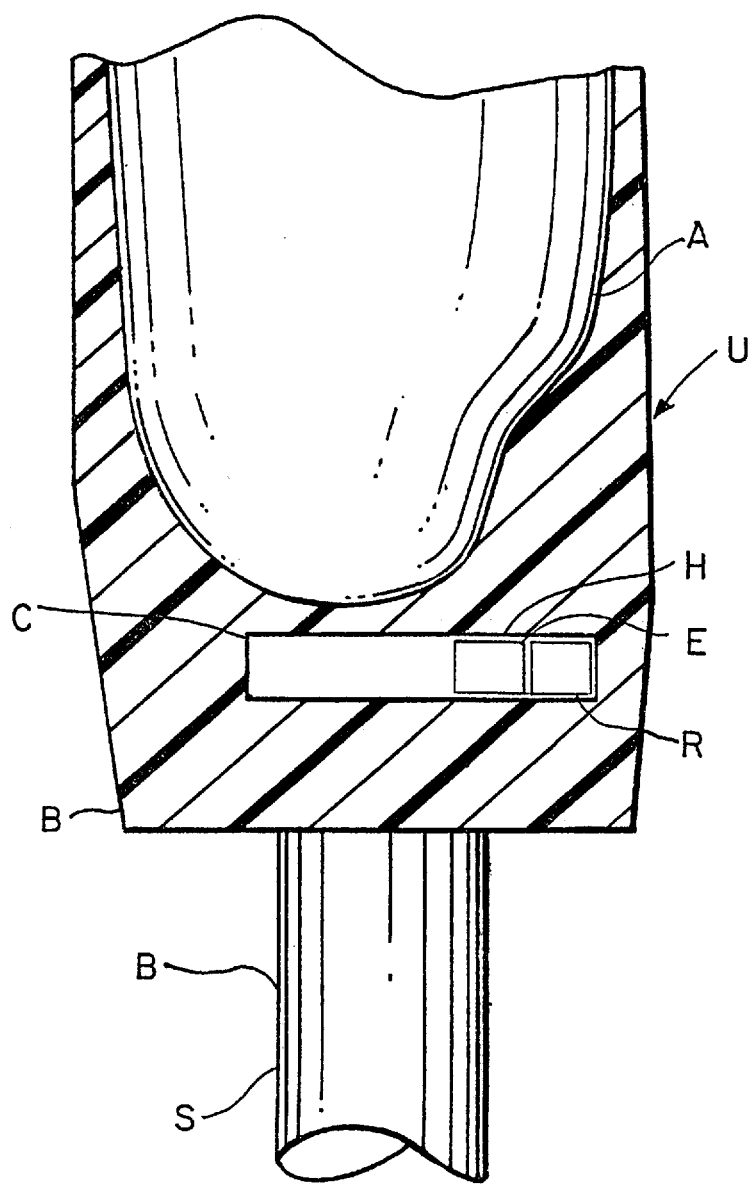
FIG. 2 is a cross-sectional view of another embodiment of a sensor device for monitoring the relative position of a residual portion of an amputee's leg relative to a prosthetic device connected to the amputee's leg.

The embodiment shown in FIG. 2 differs from the embodiment in FIG. 1 because the battery power supply E, the proximity sensor C and the alarm R are all integrated on a single device enclosed by Housing H which is held in the prosthetic device B or attached to the upper member U of the prosthetic device B near the residual portion A. This has the advantage that the connecting cable line L is eliminated.

Figure 3:
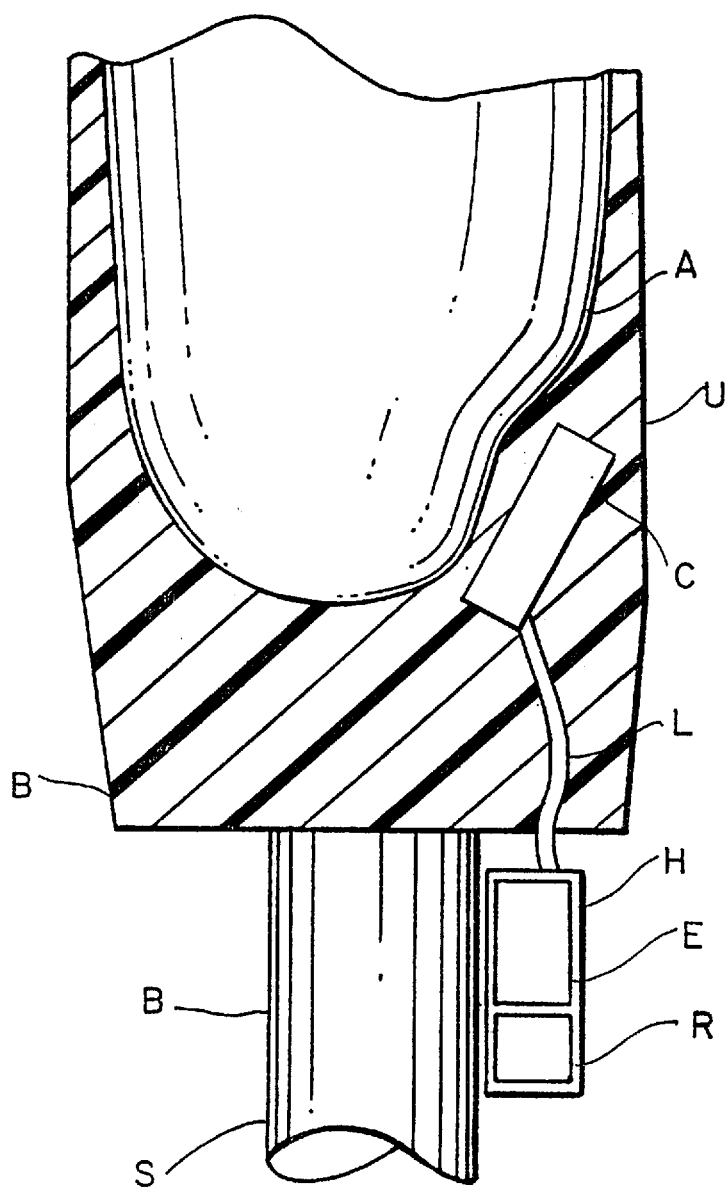
FIG. 3 is a cross-sectional view of an additional embodiment of a sensor device for monitoring the relative position of a residual portion of an amputee's leg relative to a prosthetic device connected to the amputee's leg.

The embodiment of FIG. 3 is a variant of the embodiment of FIG. 1 in which the proximity sensor C is placed adjacent to an area of potential located laterally or displaced from the center to the side of the upper member U of the prosthetic device.

Figure 4:
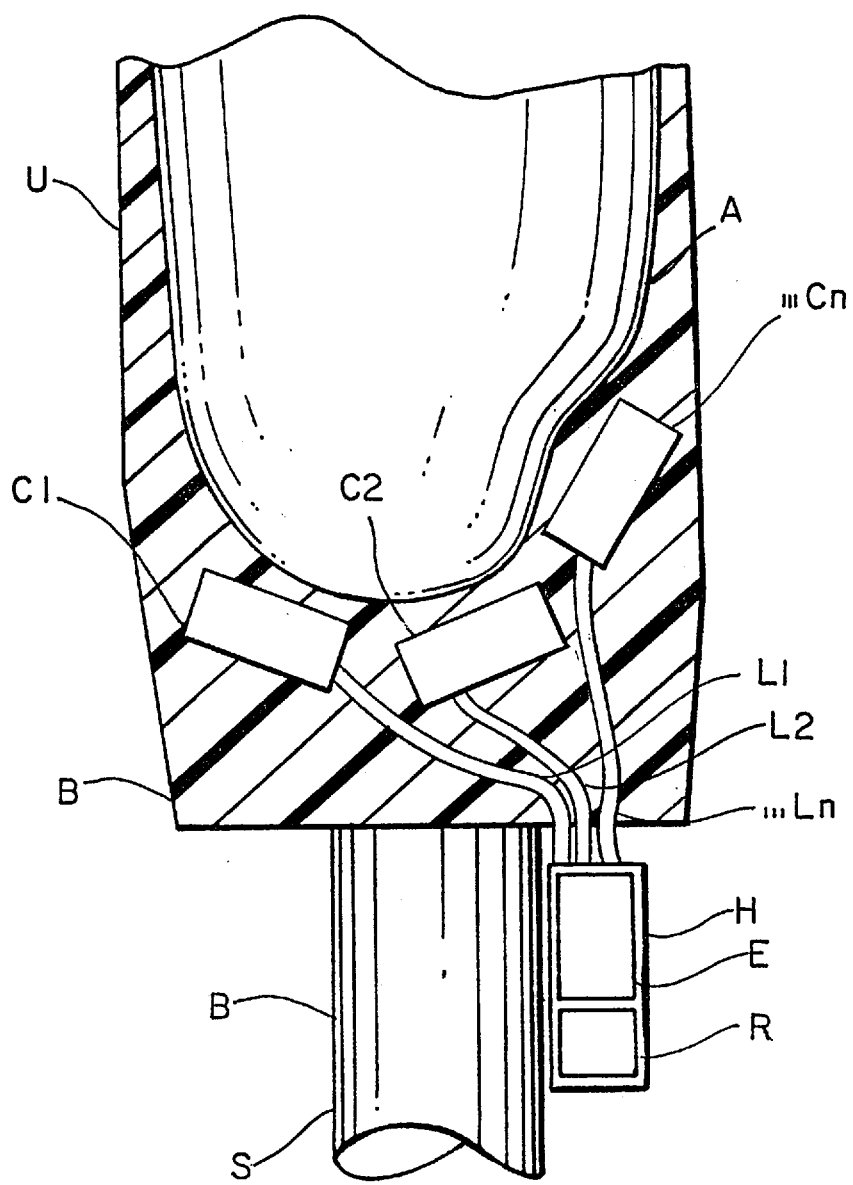
FIG. 4 is a cross-sectional view of an additional embodiment of multiple sensor devices for monitoring the relative position of a residual portion of an amputee's leg relative to a prosthetic device connected to the amputee's leg.

The embodiment of FIG. 4 is a variant of the embodiment of FIG. 1 in which the multiple proximity sensors C1, C2, . . . , Cn are located in the upper member U of the prosthetic device adjacent to areas of potential injury and connected to the remote battery power supply E by individual cable lines L1, L2, . . . , Ln.

Figure 5:
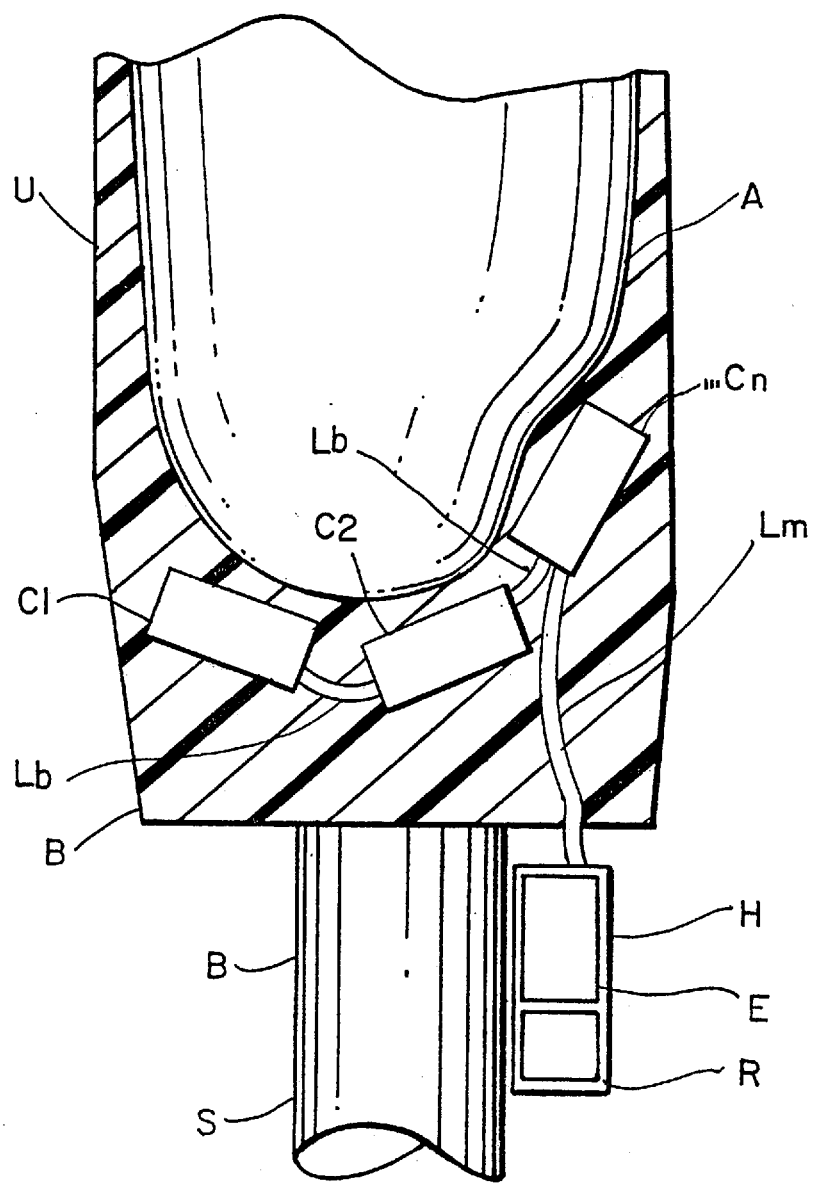
FIG. 5 is a cross-sectional view of an additional embodiment of multiple sensor devices for monitoring the relative position of a residual portion of an amputee's leg relative to a prosthetic device connected to the amputee's leg.

The embodiment of FIG. 5 is a variant of the embodiment of FIG. 4 in which the multiple proximity sensors C1, C2, . . . , Cn are connected to the remote battery power supply E by a continuos cable system, with cable line Lb connecting the individual sensors together, and cable line Lm connecting the system to the remote battery power supply E and alarms means R.

The proximity sensor C in the above embodiments can be a commercially obtained proximity sensor or a specially made customized proximity sensor. It can be either a photoelectric sensor, or a capacitive sensor or an ultrasonic sensor. Such sensors are well known and standard automation components.

The alarm means can include means for making an audible tone or sound. This type of sound generating means is well known and often used in alarms. It can also include means for generating a visual signal or a combination of an aural signal and visual signal.

While the invention has been illustrated and described as embodied in a sensor device for monitoring a relative position of a prosthetic device fitted to a residual portion of a limb of an amputee, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A sensor device for monitoring a relative position of prosthetic device fitted to a residual portion of a limb of an amputee with respect to the residual portion of the limb, said sensor device comprising a battery power supply, proximity sensor means for generating a position signal indicative of a relative position of said prosthetic device with respect to said residual portion without contact with said residual portion, said proximity sensor means being held in said prosthetic device at a position adjacent said residual portion and being electrically connected to the battery power supply, and an alarm means for signaling the amputee when the prosthetic device is located in said at least one position.

2. The sensor device as defined in claim 1, wherein said proximity sensor means set point is adjusted to result in a change in signal state when said residual portion takes said at least one position with respect to said prosthetic device in which said residual portion could be injured, wherein the said signal state change results in the desired alarm warning.

3. The sensor device as defined in claim 1, wherein the battery power with the alarm means are mounted on the prosthetic device near the proximity sensor means.

4. The sensor device as defined in claim 3, wherein said prosthetic device comprises an upper member and a stem and said proximity sensor means is embedded in said upper member near to said residual portion, and said battery power supply with alarm means are attached to said stem together in the vicinity of said upper member and connected with said proximity sensor means via a cable line.

5. The sensor device as defined in claim 4, wherein said proximity sensor means is located in a center of said upper member.

6. The sensor device as defined in claim 4, wherein said proximity sensor means is located laterally displaced from a center of said upper member.

7. The sensor device as defined in claim 4, comprised of multiple proximity sensor means placed in locations adjacent to areas of potential injury and where monitoring to avoid such injury is beneficial, wherein said proximity sensor means each have an individual cable conductor to the said battery power supply means with said alarm means.

8. The sensor device as defined in claim 7, wherein said proximity sensor are interconnected by a continuos cable conductor to the said battery power supply means with said alarm means.

9. The sensor device as defined in claim 1, wherein said proximity sensor means, said battery power supply with said alarm means, comprise a single integrated unit being located in said prosthetic device in the vicinity of said residual portion.

10. The sensor device as defined in claim 1, wherein said proximity sensor means comprises one or more of a photoelectric sensor, a capacitive sensor and an ultrasonic sensor.

11. The sensor device as defined in claim 8, wherein said photoelectric sensor is one of an Infra Red diode sensor and a laser diode sensor.

* * * * *